US012773471B2

(12) United States Patent
Ghodbane

(10) Patent No.: US 12,773,471 B2
(45) Date of Patent: Oct. 27, 2026

(54) MEDICAL SEALANTS

(71) Applicant: Ethicon, Inc., Raritan, NJ (US)

(72) Inventor: Salim A. Ghodbane, Piscataway, NJ (US)

(73) Assignee: Ethicon, Inc., Raritan, NJ (US)

( * ) Notice: Subject to any disclaimer, the term of this patent is extended or adjusted under 35 U.S.C. 154(b) by 650 days.

(21) Appl. No.: 18/178,837

(22) Filed: Mar. 6, 2023

(65) Prior Publication Data

US 2024/0299617 A1 Sep. 12, 2024

(51) Int. Cl.
*A61L 24/04* (2006.01)
*A61L 24/00* (2006.01)

(52) U.S. Cl.
CPC ......... *A61L 24/043* (2013.01); *A61L 24/0042* (2013.01)

(58) Field of Classification Search
None
See application file for complete search history.

(56) References Cited

U.S. PATENT DOCUMENTS 5,874,500 A 2/1999 Rhee
6,458,889 B1 10/2002 Trollsas et al.
8,987,339 B2 3/2015 Askari
9,463,004 B2 10/2016 Campbell
10,227,289 B2 3/2019 Askari
2009/0196928 A1 8/2009 Hnojewyi
2010/0297235 A1 11/2010 Hnojewyi
2013/0345334 A1* 12/2013 Hoogenboom .......... C08J 3/246 523/105
2014/0114350 A1* 4/2014 Sargeant ............... A61L 31/148 606/213
2014/0228453 A1* 8/2014 Bennett ..................... A61P 1/00 514/772.6
(Continued)

FOREIGN PATENT DOCUMENTS

WO 2012035598 A1 3/2012
WO 2019114108 A1 6/2019
WO 2021014446 A1 1/2021

OTHER PUBLICATIONS

International Search Report & Written Opinion for corresponding PCT Application No. PCT/IB2024/051445, dated May 8, 2024.

*Primary Examiner* — Jeffrey D Washville
(74) *Attorney, Agent, or Firm* — David R. Crichton

(57) ABSTRACT

Disclosed is a sealant, and techniques for making and using the sealant. The sealant may include three components that, when combined, produce the sealant: an electrophilic component, a nucleophilic component, and a doping component. The electrophilic component may include a first electrophilic material having a first functionality of a first reactive group. The nucleophilic component may include a first nucleophilic material having a second functionality of a second reactive group. The doping component may include a second electrophilic material having a third functionality of the first reactive group greater than the first functionality and/or a second nucleophilic material having a fourth functionality of the second reactive group greater than the second functionality. The doping component may be present in an amount sufficient to provide a 2-20% molar contribution of the first reactive group and/or the second reactive group in the sealant.

19 Claims, 7 Drawing Sheets

(56) References Cited

U.S. PATENT DOCUMENTS

| | | | | |
|---|---|---|---|---|
| 2014/0271528 | A1 * | 9/2014 | Askari | A61P 17/02<br>524/879 |
| 2014/0302051 | A1 | 10/2014 | Askari | |
| 2019/0269818 | A1 | 9/2019 | Dhanaraj | |
| 2019/0269819 | A1 | 9/2019 | Dhanaraj | |
| 2020/0332161 | A1 * | 10/2020 | Chung | A61L 24/06 |

* cited by examiner

MEDICAL SEALANTS

FIELD OF THE INVENTION

The invention relates to multi-component sealants for medical use.

BACKGROUND

Medical sealants are used as an adjunct to primary closures with, for example, sutures, surgical meshes, and staples. Medical sealants, such as lung sealants, blood vessel sealants, etc., are used to prevent leakage of blood, air, or other bodily fluid after surgery or injury. Sealants are particularly important for preventing complications after surgery, including, e.g., infections.

Medical sealants typically involve one or more materials adhering to a location on the body by curing or gelling in place after application. However, use of such sealants can be challenging if movement occurs after application but before the sealant cures or gels. Thus, in addition to other desirable performance characteristics (e.g., high tensile strength, high elongation at failure, and a low elastic modulus), medical sealants also preferably have a very low curing or gelation time.

Conventional sealants have, to date, failed to provide all of the desired performance characteristics for medical sealants.

BRIEF SUMMARY

Various deficiencies in the prior art are addressed below by the disclosed compositions of matter and techniques.

In some embodiments, a sealant may be provided. The sealant may include three components that, when combined, produce the sealant: an electrophilic component, a nucleophilic component, and a doping component. The electrophilic component may include a first electrophilic material (such as a polymer or biological material) having a first functionality of a first reactive group. The nucleophilic component may include a first nucleophilic material (such as a polymer or biological material) having a second functionality of a second reactive group. The doping component may include a second electrophilic material (such as a polymer or biological material) having a third functionality of the first reactive group greater than the first functionality and/or a second nucleophilic material (such as a polymer or biological material) having a fourth functionality of the second reactive group greater than the second functionality. The doping component may be present in an amount sufficient to provide a 2-20% molar contribution of the first reactive group and/or the second reactive group in the sealant.

In some embodiments, the first nucleophilic polymer may include a first multi-arm nucleophilic PEG, which may be bioabsorbable in vivo. The first multi-arm nucleophilic PEG may be a PEG-Amine, such as 4-arm PEG-NH2-HCl. The second nucleophilic polymer may be a second multi-arm nucleophilic PEG, which may be bioabsorbable in vivo. The second multi-arm nucleophilic PEG may be, e.g., a 6- and/or 8-arm PEG-NH2-HCl.

In some embodiments, the first electrophilic polymer may include a first multi-arm electrophilic PEG, which may be bioabsorbable in vivo. The first multi-arm electrophilic PEG may be a PEG-NHS Ester, such as 4-arm PEG-succinimidyl glutarate (SG). The second electrophilic polymer may be a second multi-arm electrophilic PEG, which may be bioabsorbable in vivo. The second multi-arm electrophilic PEG may be, e.g., a 6- and/or 8-arm PEG-SG.

In some embodiments, the sealant (such as the electrophilic component, the nucleophilic component, and/or the doping component) may include an additive. In some embodiments, the additive may be an antioxidant, such as tocopherol or a derivative thereof. In some embodiments, the antioxidant may be α-tocopherol, β-tocopherol, γ-tocopherol, δ-tocopherol, tocotrienol, or a combination thereof. In some embodiments, the additive may be a colorant, such as FD&C Bluc #1, FD&C Bluc #2, FD&C Green #3, FD&C Yellow #6, or a combination thereof. In some embodiments, the additive may be a contrast agent.

In some embodiments, the electrophilic component may include an acidic buffer for reconstituting the first electrophilic polymer, and the nucleophilic component further comprises an alkaline buffer for reconstituting the first nucleophilic polymer. In various embodiments, the pKa of the buffer for reconstituting the first nucleophilic polymer may be about 7.9 pKa to about 9.7 pKa. In various embodiments, the pH of the nucleophilic component after reconstitution of the buffer for the first nucleophilic polymer may be at least 0.05 pH units above the buffer pKa. In various embodiments, the nucleophilic component has a pH after reconstitution of about 9.0 to about 10.5. In various embodiments, the buffer for reconstituting the first electrophilic polymer may have a concentration of about 3.5 mM to about 15 mM and may have a pH prior to reconstitution of about 4.0 to about 7.0. In various embodiments, the buffer for reconstituting the first electrophilic polymer may have a pH prior to reconstitution of about 4.0 to less than 5.0.

In some embodiments, the final concentrations of the first nucleophilic polymer and the first electrophilic polymer in the sealant are each about 39 mg/mL to about 87 mg/mL, and wherein the first nucleophilic polymer, the second nucleophilic polymer, the first electrophilic polymer, and the second electrophilic polymer each have a molecular weight of about 20 kDa.

In some embodiments, a system may be provided. The system may include a sealant as disclosed herein, and an applicator having an applicator body configured to hold a first component of the sealant in a first volume of space and hold a second component of the sealant in a second volume of space separate from the first volume of space, the applicator configured to allow the first component and second component to be combined. The first component may include the electrophilic component and optionally at least a part of the doping component. The second component may include the nucleophilic component and optionally at least a part of the doping component.

In some embodiments, a kit may be provided. The kit may include multiple storage containers. The kit may include a first storage container including a dry first nucleophilic polymer powder. The kit may include a second storage container including an alkaline buffer for preparing a first electrophilic polymer composition. The kit may include a third storage container including a dry first electrophilic polymer powder. The kit may include a fourth storage container including an acidic buffer for preparing a first electrophilic polymer composition. The kit may include at least one additional container. The at least one additional container may be a storage container including a dry second nucleophilic polymer powder and/or a storage container including a dry second electrophilic polymer powder. The sealant is formed after combining the first nucleophilic polymer composition and first electrophilic polymer composition.

In some embodiments, a method of using a sealant may be provided. The scalant may be formed by combining a first nucleophilic polymer composition with a first electrophilic polymer composition and allowing the sealant to cure. The sealant may be an embodiment of a sealant as disclosed herein.

The method may include forming the first nucleophilic polymer composition by adding an alkaline buffer to the first nucleophilic polymer. The method may include forming the first electrophilic polymer composition by adding an acidic buffer to the first electrophilic polymer. In some embodiments, forming the first nucleophilic polymer composition may also include adding the second nucleophilic polymer, and/or forming the first electrophilic polymer composition may also include adding the second electrophilic polymer.

In some embodiments, the method may include adding an antioxidant to the first nucleophilic polymer composition and/or the first electrophilic polymer composition. In some embodiments, the method may include irradiating the first nucleophilic polymer composition and/or the first electrophilic polymer composition, which may include X-ray irradiation up to about 40 kiloGrays (kGy). In some embodiments, a 4-arm PEG-Amine, a 4-arm PEG-NHS ester, and a 6- or 8-arm PEG-Amine and/or PEG-NHS ester are irradiated under a low oxygen environment and the 4-arm PEG-Amine and any 6- or 8-arm PEG-Amine is in a protonated form. In various embodiments, forming a sealant may include using an applicator device to mix and simultaneously apply the first nucleophilic polymer composition and the first electrophilic polymer composition onto a substrate, such as tissue of a patient.

In some embodiments, a method of making a sealant may be provided. The method may include forming an electrophilic polymer composition by mixing an alkaline buffer with a first electrophilic polymer having a first functionality of a first reactive group and optionally a second electrophilic polymer having a second functionality of the first reactive group that is greater than the first functionality, and separately forming a nucleophilic polymer composition by mixing an acidic buffer with a first nucleophilic polymer having a third functionality of a second reactive group and optionally a second nucleophilic polymer having a fourth functionality of the second reactive group that is greater than the third functionality. The electrophilic polymer composition should contain the second electrophilic polymer and/or the nucleophilic polymer composition should contain the second nucleophilic polymer. The method may include simultaneously delivering the electrophilic polymer composition and nucleophilic polymer composition with an applicator device that provides adequate mixing of the electrophilic polymer composition and nucleophilic polymer composition onto a substrate, and then allowing the sealant to cure on the substrate.

In some embodiments, the first electrophilic polymer may be a 4-arm PEG, the second electrophilic polymer may be a 6- and/or 8-arm PEG, the first nucleophilic polymer may be a 4-arm PEG, and the second nucleophilic polymer may be a 6- and/or 8-arm PEG. In some embodiments, the first electrophilic polymer, the second electrophilic polymer, the first nucleophilic polymer, and the second nucleophilic polymer may be bioabsorbable in vivo.

In some embodiments, the first nucleophilic polymer and any second nucleophilic polymer may be irradiated prior to mixing with the alkaline buffer and the first electrophilic polymer, and any second electrophilic polymer is irradiated prior to mixing with the acidic buffer.

In some embodiments, the method may include adding 730 ppm to about 3000 ppm of a colorant to the first electrophilic polymer wherein the first electrophilic polymer is in the form of a dry powder prior to mixing the first electrophilic polymer with the acidic buffer.

In some embodiments, the first nucleophilic polymer may be in the form of a dry powder and at least about 65% of the first nucleophilic polymer in the dry powder form have a particle size of about 250 microns to about 1250 microns. In some embodiments, the first nucleophilic polymer may be in the form of a dry powder and at least about 20% of the first nucleophilic polymer in the dry powder form have a particle size of greater than 710 microns. In some embodiments, the first electrophilic polymer may be in the form of a dry powder and at least about 80% of the first electrophilic polymer in the dry powder form have a particle size of about 250 microns to about 1250 microns. In some embodiments, the first electrophilic polymer may be in the form of a dry powder and at least about 40% of the first electrophilic polymer in the dry powder form have a particle size of greater than 500 microns.

In some embodiments, a pKa of the acidic buffer for the nucleophilic polymer composition may be about 7.9 pKa to about 9.7 pKa. In some embodiments, the pH of the nucleophilic polymer composition may be at least 0.05 pH units above the pKa of the acidic buffer. In some embodiments, the nucleophilic polymer composition may have a pH after reconstitution of about 9.0 to about 10.5. In some embodiments, the alkaline buffer for the nucleophilic polymer composition may have a concentration of about 180 mM to about 220 mM and a pH prior to reconstitution of about 9.34 to about 9.76. In some embodiments, the acidic buffer for the electrophilic polymer composition may have a concentration of about 3.5 mM to about 15 mM and a pH prior to reconstitution of about 4.0 to about 5.0.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

Figure 1:
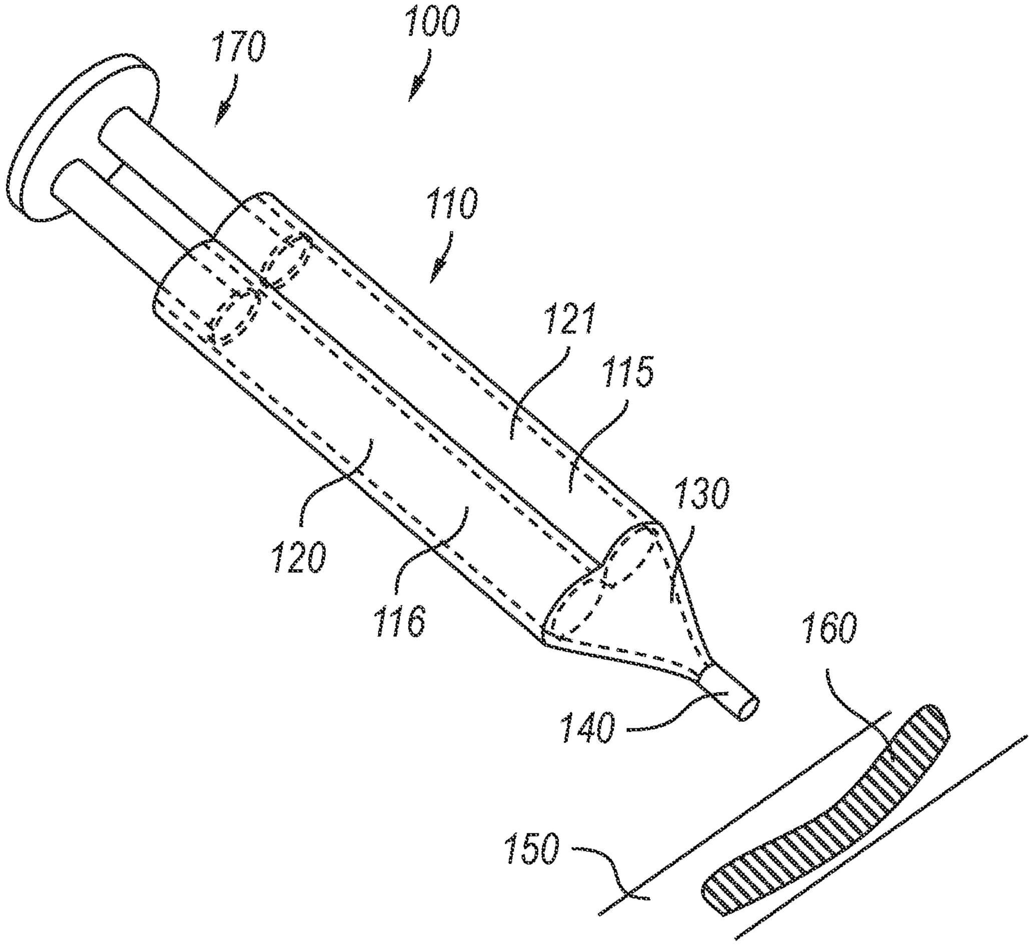
FIGS. 1 and 2 are illustration of a various embodiments of a system.

It will be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION

In various applications, a sealant is used to stop a fluid (e.g., a liquid, gas, etc.) from flowing past or through an opening. To do so requires the sealant to provide certain essential mechanical properties, which may vary depending on the specific application. While use of some modifiers is known to improve cure rates, such improvements come with a cost, typically in the form of reduced mechanical properties. The disclosed sealants provide enhanced gelation or cure rates while maintaining essential mechanical properties.

Specifically, the disclosed sealants surprisingly and unexpectedly have advantageous polymerization times and polymerizations rates for, e.g., a medical sealant, while also maintaining a desirable range of mechanical properties, such as shear moduli. In one aspect, the sealants provided herein comprise a combination of equal molecular weight nucleophilic and electrophilic polymers, doped with an additional nucleophilic and/or electrophilic polymer having an increased functionality, as well as an optimal buffer system. Polymers having a molecular weight of about 15 kDa to about 50 kDa are preferred for use in the disclosed sealants. As used herein, the term "about [a specific number]" indicates that values within +10% of the specific number are also intended to be included. For example, "about 1" is intended to include values from 0.9-1.1.

The polymerization kinetics of the sealants provided herein can be determined as follows:

(a) Maximum shear modulus, a measure of the stiffness of the sealant;

(b) Polymerization time (k), defined as the time required to achieve 50% of the final mechanics of the sealant; and (c) Polymerization rate defined as the maximal slope of the shear modulus.

Polymerization time (k) analyzes the shear modulus over time normalized to the maximum shear modulus. Polymerization time provides an understanding of cure time (the time required to achieve final mechanics), but also allows for an indirect determination of set time, i.e., the time required for the sealant to stop flowing. Set time cannot be directly quantified as the sealant sets within a few seconds.

Polymerization rate provides a measurement of the rate at which the sealant increases in shear modulus over time. The polymerization rate is sensitive to both polymerization time and final hydrogel mechanics.

The efficacy of the sealant, or the sealant's ability to provide a strong seal, is dictated by the sealant's mechanics. The sealant mechanics are measured via cohesive tensile testing and shear modulus.

In some embodiments, a sealant may be provided. The sealant may include three components that, when combined, produce the sealant: an electrophilic component, a nucleophilic component, and a doping component (sometimes referred to as a "modifier" or a "modifying component").

The electrophilic component may include a first electrophilic polymer having a first functionality of a first reactive functional group. The nucleophilic component may include a first nucleophilic polymer having a second functionality of a second reactive functional group. Generally speaking, the first and second reactive groups are selected to interact, thereby causing the sealant to gel or cure.

For example, an amine-reactive chemical group, such as an N-hydroxysuccinimide (NHS) ester, imidoester, or maleimide, is known to form stable conjugates, i.e., amide bonds, with an amine, such as a primary, secondary, or tertiary amine. In some embodiments, the first reactive functional group (e.g., electrophilic reactive group) may be an NHS ester. Non-limiting examples of such NHS esters include succinimidyl glutarate (SG), succinimidyl valerate, succinimidyl carbonate, succinimidyl succinate, succinimidyl butanoate, succinimidyl succinamide, succinimidyl propionate, sulfosuccinimidylglutarate, sulfosuccinimidylvalerate, sulfosuccinimidylcarbonate, succinimidlyl carboxymethyl ester, sulfosuccinimidylsuccinate, sulfosuccinimidylbutanoate, sulfosuccinimidylsuccinamide, and sulfosuccinimidylpropionate. In some embodiments, the second reactive functional group (e.g., nucleophilic reactive group) may be an amine or amine salt.

In various embodiments, the first electrophilic polymer and/or the first nucleophilic polymer may be bioabsorbable in vivo. Non-limiting examples of such bioabsorbable polymers include functionalized polyethylene glycol (PEG), polycaprolactone, and polyglycolide polymers.

As used herein, the term "functionality" refers to the average number of a particular functional group per molecule. In some embodiments, the functionality ($F_F$) of the first nucleophilic polymer, first electrophilic polymer, or both is ≥1. In some embodiments, $F_F \geq 2$ for the first nucleophilic polymer, first electrophilic polymer, or both. In some embodiments $F_F \geq 3$ for the first nucleophilic polymer, first electrophilic polymer, or both. In some embodiments, $F_F \geq 4$ for the first nucleophilic polymer, first electrophilic polymer, or both. In some embodiments, $4 \leq F_F \leq 6$ for the first nucleophilic polymer, first electrophilic polymer, or both.

In some embodiments, the first electrophilic polymer and/or the first nucleophilic polymer may be a multi-arm PEG, such as a 2-, 3-, 4-, 6- or 8-arm PEG. For example, in some embodiments, the first nucleophilic polymer may be a 2-, 3-, 4-, or 6-arm PEG-Amine (such as PEG-NH2) or a PEG-Amine salt (such as PEG-NH2-HCl), and the first electrophilic polymer may be a 2-, 3-, 4-, or 6-arm PEG-NHS Ester (such as PEG-SG).

Surprisingly and unexpected, it has been found that a small amount of a doping component with an increased functionality the first functional group, a component with an increased functionality of the second functional group, or both, reduces the curing rate of the system as compared to the curing rate without this doping component.

Specifically, in some embodiments, the doping component may include a second electrophilic polymer having a third functionality of the first reactive group greater than the first functionality of the first electrophilic polymer. In some embodiments, the doping component may include a second nucleophilic polymer having a fourth functionality of the second reactive group greater than the second functionality of the first nucleophilic polymer.

In some embodiments, the functionality ($F_D$) of each doping component may, independently, be $F_D \geq 2$, $F_D \geq 3$, $F_D \geq 4$, $F_D \geq 6$, or $F_D \geq 8$. In some embodiments, $6 \leq F_D \leq 8$ for each doping component, independently.

In some embodiments, the second electrophilic polymer and/or the second nucleophilic polymer may be a multi-arm PEG, such as a 2-, 3-, 4-, 6- or 8-arm PEG. For example, in some embodiments, the second nucleophilic polymer may be a 2-, 3-, 4-, or 6-arm PEG-Amine (such as PEG-NH2) or a PEG-Amine salt (such as PEG-NH2-HCl), and the second electrophilic polymer may be a 2-, 3-, 4-, or 6-arm PEG-NHS Ester (such as PEG-SG).

As noted, any electrophilic doping component should have a higher functionality than the electrophilic polymer, and any nucleophilic doping component should have a higher functionality than the nucleophilic polymer. For example, if the first electrophilic polymer is 4-arm PEG-SG, the second electrophilic polymer used as a doping component may be a 6- or 8-arm PEG-SG. Similarly, if the first nucleophilic polymer is 4-arm PEG-NH2, the second nucleophilic polymer used as a doping component may be a 6- or 8-arm PEG-NH2.

The doping component may be present in a total amount sufficient to provide a 2-20% molar contribution of the first reactive group and/or the second reactive group in the sealant.

In some embodiments, the sealant may utilize an electrophilic component of a 4-Arm PEG (such as 4 Arm PEG-SG), a nucleophilic component of a 4-Arm PEG (such as PEG-Amine), and a doping component of 2-10% molar contribution, and preferably 2-5%, of amine groups from a 6- or 8-Arm PEG (such as a PEG-Amine) that results in a faster gelling system with equivalent mechanical performance as compared to the sealant without the doping component.

In some embodiments, the sealant may utilize an electrophilic component of a 4-Arm PEG (such as 4 Arm PEG-SG), a nucleophilic component of a 4-Arm PEG (such as PEG-Amine), and a doping component of 2-10% molar contribution, and preferably 2-5%, of electrophilic groups (such as SG groups) from a 6- or 8-Arm PEG (such as PEG-SG) that results in a faster gelling system with equivalent mechanical performance as compared to the sealant without the doping component.

In some embodiments, the nucleophilic component may utilize a biologically derived material. In some embodiments, the sealant may utilize a nucleophilic component that is a biologically derived nucleophile (such as albumin), an electrophilic component that is a 4 Arm PEG (such as PEG-SG), and a doping component of 2-10% molar contribution, and preferably 2-5%, of electrophilic groups (such as SG groups) from a 6- or 8-Arm PEG (such as PEG-SG) that results in a faster gelling system with equivalent mechanical performance as compared to the sealant without the doping component.

In some embodiments, the sealant (such as the electrophilic component, the nucleophilic component, and/or the doping component) may include an additive.

In some embodiments, the additive may be an antioxidant. Antioxidants may be added to, e.g., reduce adverse effects of any irradiation process on the sealant's polymers. In some embodiments, the antioxidant may include BHT, tocopherol, or a combination thereof. In some embodiments, the antioxidant may include α-tocopherol, β-tocopherol, γ-tocopherol, δ-tocopherol, tocotrienol, or a combination thereof. In some embodiments, antioxidants may be added at individual concentrations up to about 4000 ppm.

In some embodiments, the additive may be a colorant to, e.g., improve the visualization of the sealant against human tissue and allow for more consistent coverage of the targeted tissue. In some preferred embodiments, one or more colorants is compounded with a polymeric powder (e.g., a powder form of the first electrophilic polymer, and/or the first nucleophilic polymer, etc.). Non-limiting examples of such colorants includes FD&C Blue #1, FD&C Bluc #2, FD&C Green #3, FD&C Yellow #6, or a combination thereof. In some embodiments, antioxidants may be added at individual concentrations up to about 3000 ppm.

In some embodiments, the additive may be a contrast agent for, e.g., localizing the sealed site at a later time, or to facilitate detection by magnetic resonance imaging. In some embodiments, the contrast agent may be a non-ionic contrast agent, such as iohexol, for radiopacity. In some embodiments, the contrast agent may be a radioactive agent which allows for localization of the sealed site using radiation detection methods.

In another embodiment, the sealant may include one or more additional therapeutic agents to provide localized delivery of the therapeutic agent. For example, the therapeutic agents can be one or more chemotherapeutic agents for management of cancer.

It should also be understood that the term "therapeutic agent" herein is intended to broadly encompass various kinds of agents and medical substances, including but not limited to gene therapies, stem cell therapies, hemostatic agents, healing agents, adhesives, sealants, anti-bacterial agents, infection-resistant agents, analgesics, conventional pharmaceutical drugs, other chemicals, liquids, powders, etc. It should also be understood that the use of the term "therapeutic agent" herein is not intended to demonstrate that concepts described herein are limited to only agents that are used for therapeutic purposes. The term "therapeutic agent" as used herein is intended to encompass various kinds of medical agents/substances, including but not limited to those used for preventative, prophylactic, and/or remedial purposes, and including those used for various purposes that might not be considered "therapeutic" in a traditional sense of the word "therapeutic." Various kinds of agents/substances that may be used in accordance with the teachings herein, as well as various purposes for which such agents/substances may be used, will be apparent to those of ordinary skill in the art in view of the teachings herein. All such agents/substances/purposes are intended to be encompassed by the use of the term "therapeutic agent" herein.

In some embodiments, the electrophilic component may include an acidic buffer for reconstituting the first electrophilic polymer, and the nucleophilic component further comprises an alkaline buffer for reconstituting the first nucleophilic polymer. In various embodiments, the pKa of the buffer for reconstituting the first nucleophilic polymer may be about 7.9 pKa to about 9.7 pKa. In various embodiments, the pH of the nucleophilic component after reconstitution of the buffer for the first nucleophilic polymer may be at least 0.05 pH units above the buffer pKa. In various embodiments, the nucleophilic component has a pH after reconstitution of about 9.0 to about 10.5. In various embodiments, the buffer for reconstituting the first electrophilic polymer may have a concentration of about 3.5 mM to about 15 mM and may have a pH prior to reconstitution of about 4.0 to about 7.0. In various embodiments, the buffer for reconstituting the first electrophilic polymer may have a pH prior to reconstitution of about 4.0 to less than 5.0.

Non-limiting examples of alkaline buffers include N-cyclohexyl-2-aminoethanesulfonic acid (CHES) buffer, 2-Amino-2-methyl-1,3-propanediol, N-tris(Hydroxymethyl)methyl-4-aminobutanesulfonic acid, N-(1,1-dimethyl-2-hydroxyethyl)-3-amino-2-hydroxypropanesulfonic acid, 3-(Cyclohexylamino)-2-hydroxy-1-propanesulfonic acid, pyridoxine buffer. Non-limiting examples of acidic buffers include citrate buffers. Preferably, the acid buffer has a pH of about 4 to about 6 or up to 7.

In some embodiments, the final concentrations of the first nucleophilic polymer and the first electrophilic polymer in the sealant may each be about 39 mg/mL to about 87 mg/mL. In some embodiments, the first nucleophilic polymer, the second nucleophilic polymer, the first electrophilic polymer, and the second electrophilic polymer may each have a molecular weight of about 20 kDa, including, e.g., 18 kDa-22 kDa. In some embodiments, the first nucleophilic polymer, the second nucleophilic polymer, the first electrophilic polymer, and the second electrophilic polymer may each have a molecular weight of 15 kDa-25 kDa.

An example of a preferred first electrophilic polymer is 4-arm PEG-succinimidyl glutarate, M.W. 20 kDa (4-arm-PEG-SG-20K) (67 mg/mL) available from JenKem Technology or NOF Corporation, and an example of a preferred first nucleophilic polymer is 4-arm PEG-Amine, M.W. 20 kDa (4-arm-PEG-NH2-20K) (67 mg/mL) available from JenKem Technology or NOF Corporation.

In some embodiments, the final concentrations of the first electrophilic polymer and first nucleophilic polymer in the sealant applied to a tissue are each about 39 mg/mL to about 87 mg/mL, and preferably about 52 mg/mL to about 77 mg/mL. In some embodiments, the concentrations are each about 67 mg/mL.

In some embodiments, a system may be provided. Referring to FIG. 1, the system may include an applicator 100, which may include an applicator body 110. The applicator body may define a first internal volume of space 115 and a second internal volume of space 116 separate from the first volume of space. The applicator may be configured to hold a first component 121 of an embodiment of the sealant as disclosed herein in the first internal volume of space, and a second component 122 of an embodiment of the sealant as disclosed herein in the second internal volume of space. The first component may include the electrophilic component and optionally at least a part of the doping component of the sealant (e.g., any second electrophilic polymer) as disclosed herein. The second component may include the nucleophilic component and optionally at least a part of the doping component of the sealant (e.g., any second nucleophilic polymer) as disclosed herein.

The applicator may be configured to allow the first component and the second component to be combined. For example, in some embodiments, the applicator may include a mixing chamber 130 operably coupled to the first volume of space and the second volume of space. In some embodiments, the mixing chamber may be a static mixer within a nozzle of the applicator. The fluid forming the first component and the second component flow into the mixing chamber and then out of the mixing chamber. In some embodiments, the materials may flow out a nozzle tip 140 and onto a substrate 150.

As shown in FIG. 1, the sealant 160 forms on the substrate, and is allowed to cure. The force driving the fluid out of the volume of space may vary. For example, in some embodiments, the force is gravity. In some embodiments, a compressed gas may be applied to force the fluid out of the applicator. In some embodiments, a plunger 170 operably coupled to an end of the applicator opposite the nozzle may be used to mechanically force fluid out of the first and second volumes of space and through the nozzle.

Figure 2:
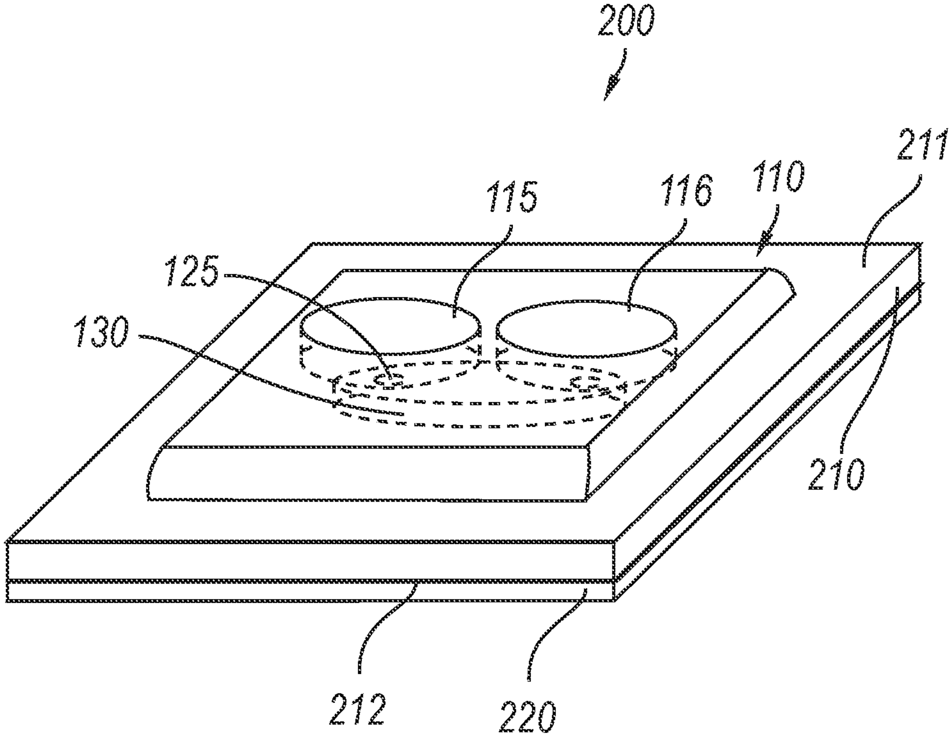

Referring to FIG. 2, an alternate embodiment can be seen, where the applicator body may be coupled to a first surface 211 of a first substrate 210 (e.g., a flexible adhesive substrate). A second substrate 220 may be removably coupled to a second surface 212 of the substrate. When the second substrate is removed, the first component and second component of the sealant may flow out of the first volume of space 115 and second volume of space 116. The components may flow through an opening 125 into a mixing chamber 130. The mixing chamber may be defined by the first substrate, or may be defined by the applicator body.

In some embodiments, a kit may be provided. The kit may include multiple storage containers. The kit may include a first storage container including a dry first nucleophilic polymer powder. The kit may include a second storage container including an alkaline buffer for preparing a first electrophilic polymer composition. The kit may include a third storage container including a dry first electrophilic polymer powder. The kit may include a fourth storage container including an acidic buffer for preparing a first electrophilic polymer composition. The kit may include at least one additional container. The at least one additional container may be a storage container including a dry second nucleophilic polymer powder and/or a storage container including a dry second electrophilic polymer powder. The sealant is formed after combining the first nucleophilic polymer composition and first electrophilic polymer composition.

Figure 3:
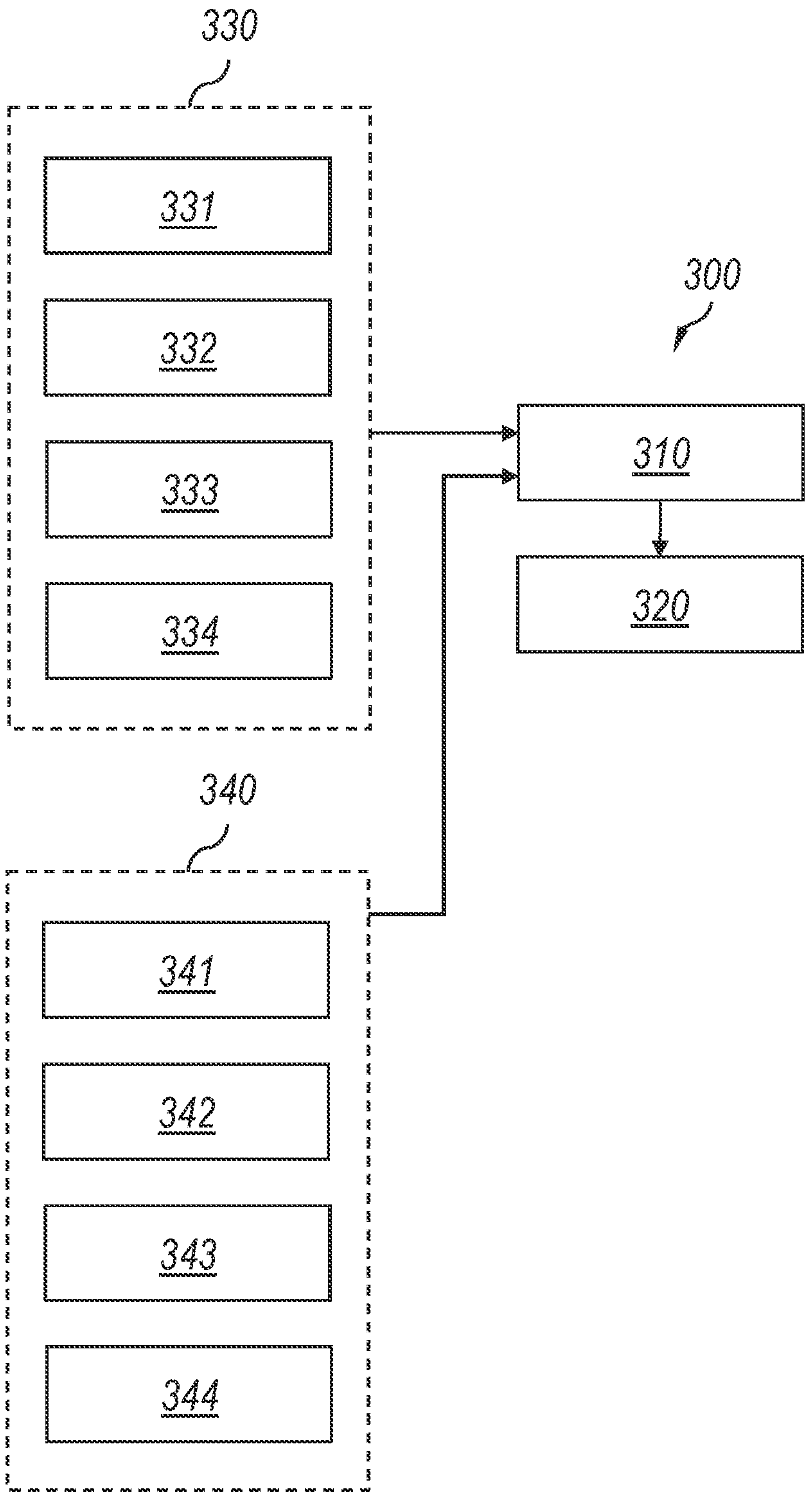
FIG. 3 is a flowchart of a method for using a sealant.

Referring to FIG. 3, in some embodiments, a method 300 of using a sealant may be provided. The method may include forming 310 the sealant by combining a first nucleophilic polymer composition with a first electrophilic polymer composition and allowing 320 the sealant to cure. The sealant may be an embodiment of a sealant as disclosed herein. In various embodiments, forming a sealant may include using an applicator device to mix and simultaneously apply the first nucleophilic polymer composition and the first electrophilic polymer composition onto a substrate, such as tissue of a patient.

In some embodiments, the method may include forming 330 the first nucleophilic polymer composition by adding 331 an alkaline buffer to the first nucleophilic polymer. In some embodiments, forming the first nucleophilic polymer composition may also include adding 332 a second nucleophilic polymer (e.g., to the first nucleophilic polymer or the mixture of the first nucleophilic polymer and the alkaline buffer).

In some embodiments, the method may include forming 340 the first electrophilic polymer composition by adding 341 an acidic buffer to the first electrophilic polymer. In some embodiments, forming the first electrophilic polymer composition may also include adding 342 the second electrophilic polymer (e.g., to the first electrophilic polymer or the mixture of the first electrophilic polymer and the acidic buffer).

In some embodiments, the method may include adding 333 an antioxidant to the first nucleophilic polymer composition and/or adding 343 an antioxidant to the first electrophilic polymer composition.

In some embodiments, the method may include irradiating 334 the first nucleophilic polymer composition and/or irradiating 344 the first electrophilic polymer composition, which may include X-ray irradiation up to about 40 kiloGrays (kGy). In some embodiments, a 4-arm PEG-Amine, a 4-arm PEG-NHS ester, and a 6- or 8-arm PEG-Amine and/or PEG-NHS ester are irradiated under a low oxygen environment and the 4-arm PEG-Amine and any 6- or 8-arm PEG-Amine is in a protonated form.

Figure 4:
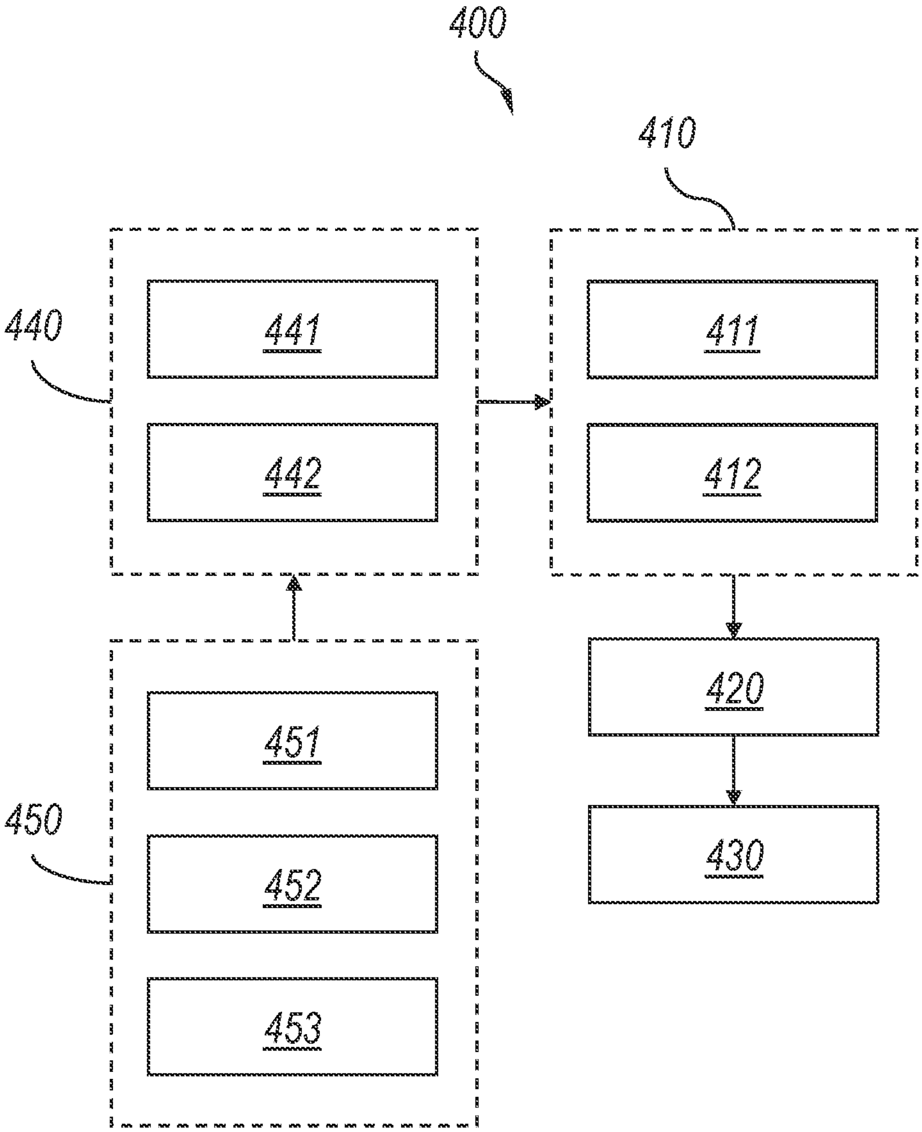
FIG. 4 is a flowchart of a method for making a sealant.

Referring to FIG. 4, in some embodiments, a method 400 of making a sealant may be provided. The method may include forming 410 an electrophilic polymer composition by mixing 411 an alkaline buffer with a first electrophilic polymer having a first functionality of a first reactive group and optionally a second electrophilic polymer having a second functionality of the first reactive group that is greater than the first functionality. The method may include separately forming 412 a nucleophilic polymer composition by mixing an acidic buffer with a first nucleophilic polymer having a third functionality of a second reactive group and optionally a second nucleophilic polymer having a fourth functionality of the second reactive group that is greater than the third functionality. The electrophilic polymer composition should contain the second electrophilic polymer and/or the nucleophilic polymer composition should contain the second nucleophilic polymer.

In some embodiments, the first electrophilic polymer may be a 4-arm PEG, the second electrophilic polymer may be a 6- and/or 8-arm PEG, the first nucleophilic polymer may be a 4-arm PEG, and the second nucleophilic polymer may be a 6- and/or 8-arm PEG. In some embodiments, the first electrophilic polymer, the second electrophilic polymer, the first nucleophilic polymer, and the second nucleophilic polymer may be bioabsorbable in vivo.

In some embodiments, the first nucleophilic polymer may be in the form of a dry powder and at least about 65% of the first nucleophilic polymer in the dry powder form have a particle size of about 250 microns to about 1250 microns. In some embodiments, the first nucleophilic polymer may be in the form of a dry powder and at least about 20% of the first nucleophilic polymer in the dry powder form have a particle size of greater than 710 microns. In some embodiments, the first electrophilic polymer may be in the form of a dry powder and at least about 80% of the first electrophilic polymer in the dry powder form have a particle size of about 250 microns to about 1250 microns. In some embodiments, the first electrophilic polymer may be in the form of a dry powder and at least about 40% of the first electrophilic polymer in the dry powder form have a particle size of greater than 500 microns.

In some embodiments, a pKa of the acidic buffer for the nucleophilic polymer composition may be about 7.9 pKa to about 9.7 pKa. In some embodiments, the pH of the nucleophilic polymer composition may be at least 0.05 pH units above the pKa of the acidic buffer. In some embodiments, the nucleophilic polymer composition may have a pH after reconstitution of about 9.0 to about 10.5. In some embodiments, the alkaline buffer for the nucleophilic polymer composition may have a concentration of about 180 mM to about 220 mM and a pH prior to reconstitution of about 9.34 to about 9.76. In some embodiments, the acidic buffer for the electrophilic polymer composition may have a concentration of about 3.5 mM to about 15 mM and a pH prior to reconstitution of about 4.0 to about 5.0.

The method may include simultaneously delivering 420 the electrophilic polymer composition and nucleophilic polymer composition with an applicator device that provides adequate mixing of the electrophilic polymer composition and nucleophilic polymer composition onto a substrate, and then allowing 430 the sealant to cure on the substrate.

In some embodiments, the polymers may be irradiated 440. In some embodiments, the method may include irradiating 441 the first nucleophilic polymer and any second nucleophilic polymer prior to mixing with the alkaline buffer. In some embodiments the method may include irradiating 442 the first electrophilic polymer and any second electrophilic polymer prior to mixing with the acidic buffer.

In some embodiments, the method may include introducing 450 an additive to a composition. In some embodiments, the method may include adding 451 a colorant, such as from 730 ppm to about 3000 ppm of a colorant, to the first electrophilic polymer wherein the first electrophilic polymer is in the form of a dry powder prior to mixing the first electrophilic polymer with the acidic buffer. In some embodiments, the method may include adding 452 an antioxidant to a composition. In some embodiments, the method may include adding 453 a contrast agent to a composition. These additions may be done before or after any irradiation (if used).

Example 1

Effect of Doping on Burst Pressure

Figure 5:
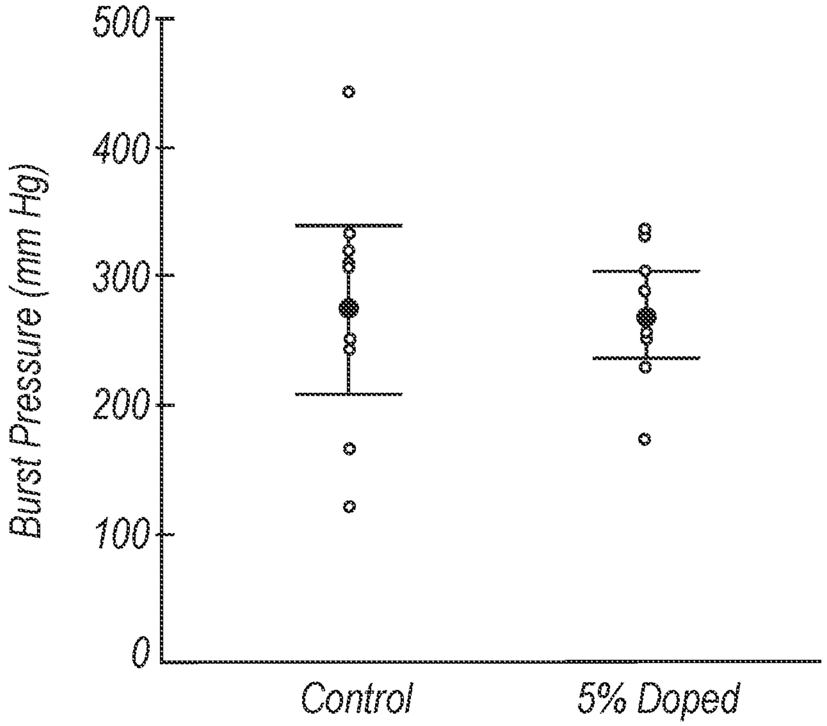
FIG. 5 is a graph showing burst pressure measurements for a control sealant vs an embodiment of a sealant as disclosed herein.

To investigate the effect of high functionality doping on mechanics, a burst pressure test was performed on porcine pleura tissue. The control was a combination of a 62 mg/mL. 20 kDa 4-Arm PEG-SG, 62 mg/mL 20 kDa 4-Arm PEG-Amine, and 100 mM CHES (pH=9.35). The exemplary formulation tested was a 5% mol contribution high functionality formulation, which consisted of a 62 mg/mL, 20 kDa 4-Arm PEG-SG, 59.85 mg/mL 4 Arm 20 kDa PEG-Amine-HCl, a 100 mM CHES (pH=9.35), and 1.575 mg/mL 20 kDa 8-Arm Peg-AmineHCl. As seen in FIG. 5, there was no significant difference between the control and 5% doped formulations (p=0.873, 2-sample t-test).

Example 2

Effect of Doping Concentration of Electrophilic Groups on Travel Distance

For a sealant, travel distance can be considered an easily measured proxy for cure time. To determine the effect of doping concentration on travel distance, various formulas were compared to a control. The different nucleophilic and electrophilic polymer concentrations can be seen in Table 1, below.

TABLE 1

Formulations For Testing Effect Of Doping Concentration of Electrophilic Groups on Travel Distance

| Formula | 4-Arm PEG-Amine-10k mg/mL (mM) | 4-Arm PEG-SG-20k mg/mL (mM) | 8-Arm PEG-SG mg/mL (mM) |
|---|---|---|---|
| Control | 28.5 (2.85) | 75 (3.75) | 0 (0) |
| 2% Doping | 28.5 (2.85) | 73.5 (3.675) | 0.75 (0.375) |
| 5% Doping | 28.5 (2.85) | 71.25 (3.5625) | 1.875 (0.09375) |
| 10% Doping | 28.5 (2.85) | 67.5 (3.375) | 3.75 (0.1875) |
| 20% Doping | 28.5 (2.85) | 60 (3) | 7.5 (0.375) |
| 50% Doping | 28.5 (2.85) | 37.5 (1.875) | 18.75 (0.9375) |

As shown, in this study, the pure 4 Arm formulation was 75 mg/mL 4 Arm PEG-SG-20 k, 28.5 mg/mL 4-Arm PEG-Amine-10 k, with a 50 mM carbonate buffer (pH=10.25). The various exemplary formulas were created by varying the amounts of 8-Arm PEG-SG 20 k up to 50% of the SG groups being contributed by the 8-Arm PEG. The 4-Arm PEG-SG-20 k concentration was adjusted to maintain a constant molarity of reactive groups. Immediately before testing, the PEG-SG was dissolved in 5 mL of 50 mM carbonate buffer at pH 9.0 and tested for travel distance on a 30-degree incline plane using an EVICEL fibrin sealant device and control tip.

Figure 6:
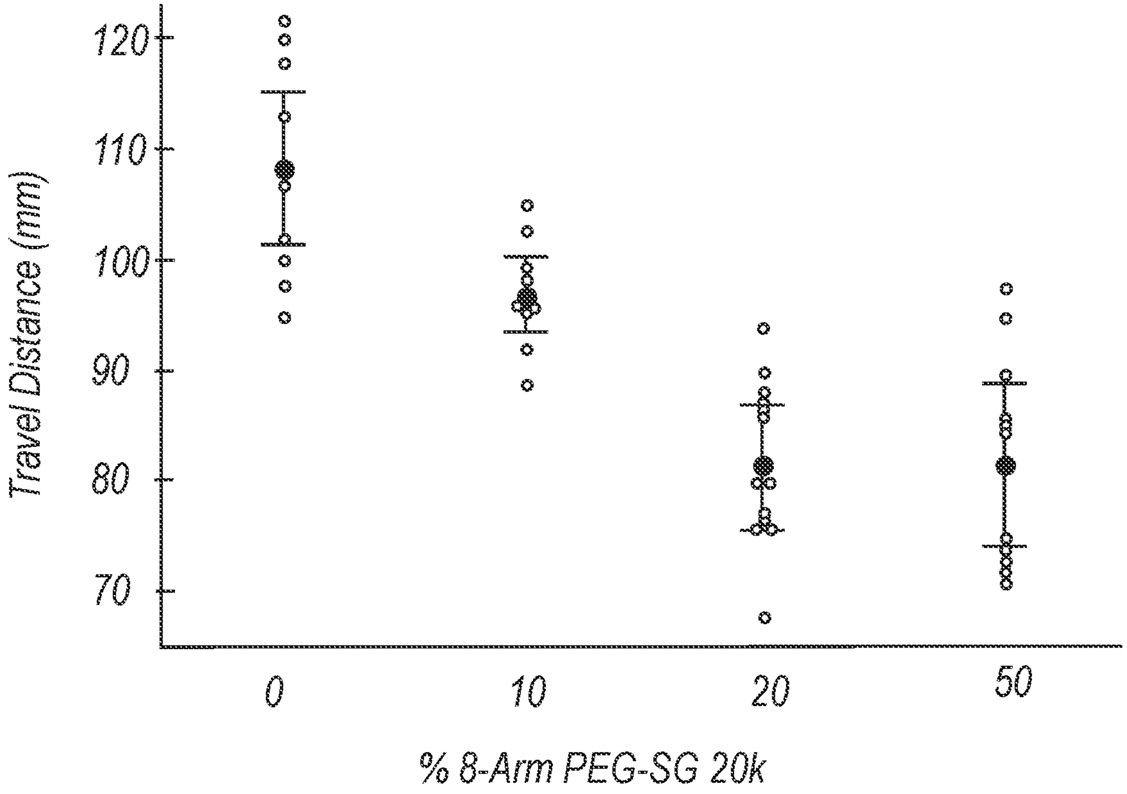
FIGS. 6 and 7 are graphs showing travel distance measurements for a control sealant vs embodiments of a sealant as disclosed herein.

Referring to FIG. 6, in a first comparison, 10%, 20%, and 50% doping formulations were compared to the control formulation. There was a significant effect on travel distance caused by the addition of 8-Arm PEG-SG formulation (p=0.000, one-way ANOVA). There was a significant difference between the replicates with 0%, 10%, and 20% and 50% 8-Arm PEG-SG 20 k. Travel distances were not statistically different between 20% and 50% 8-Arm samples.

Thus, there was a statistically significant reduction in cure times for the 10%, 20%, and 50% doping formulations as compared to the control formulation.

Figure 7:
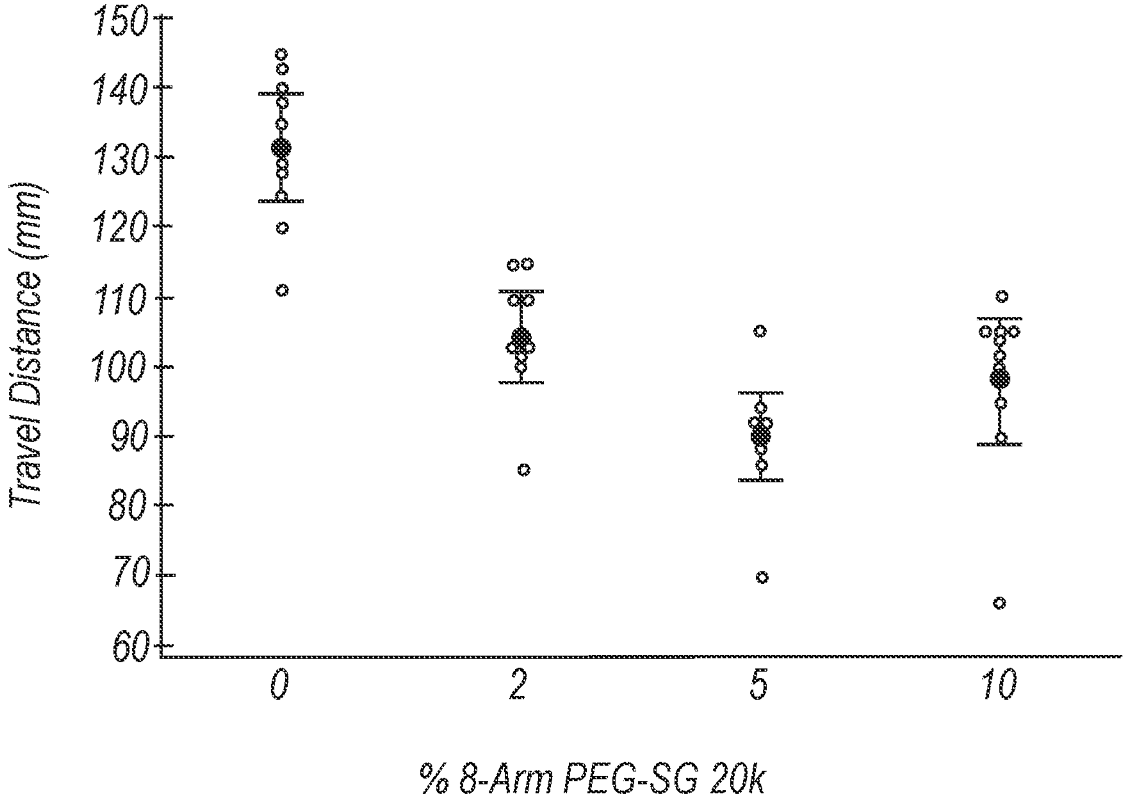

Referring to FIG. 7, in a second comparison, 10%, 5%, and 2% doping formulations were compared to the control formulation. As seen, even when the molar contribution of 8-Arm PEG-SG-20 k was decreased as low as 2%, there was still a statistically significant effect on travel distance (p=0.000, one-way ANOVA). Indeed, there was a significant difference between 0% percent and 2%, 5%, and 10%. However, there were no significant difference between 2% and 10%. Thus, there was a statistically significant reduction in cure times for the 2%, 5%, and 10% doping formulations as compared to the control formulation.

Example 3

Effect of Doping Concentration of Nucleophilic Groups

In this study, to test the impact of doping nucleophilic groups on certain sealant properties, varying amounts of 4-Arm PEG-Amine and 8-Arm PEG-AmineHCl 20 k were added to 4-Arm PEG-SG-20K with a constant molar ratio of reactive groups. The PEG-Amines were dissolved in 200 mM CHES (pH=9.35). Immediately before testing, 62 mg/mL 4 Arm PEG-SG-20 k was prepared in water. The sealants were loaded into a dual syringe device and expressed with static mixing tip into a weigh boat. After curing, the resulting gels were all then inspected. The different nucleophilic and electrophilic polymer concentrations can be seen in Table 2, below.

TABLE 2

Formulations For Testing Effect Of Doping Concentration of Nucleophilic Groups.

| Formula | 4-Arm PEG-SG-20k mg/mL | 4-Arm PEG-Amine-20k mg/mL | 8-Arm PEG-AmineHCl-20k mg/mL |
|---|---|---|---|
| Control | 62 | 62 | 0 |
| 2% Doping | 62 | 55.76 | 0.62 |
| 5% Doping | 62 | 53.9 | 1.55 |
| 10% Doping | 62 | 50.8 | 3.1 |
| 20% Doping | 62 | 44.6 | 6.2 |
| 50% Doping | 62 | 26 | 15.5 |

All resulting gels could be easily removed from the weigh boat and appeared fully reacted. As the contribution of 8-Arm PEG increased from 0 to 10%, the gels became somewhat stiffer but remained quite flexible. In addition, the gels could be stretched without breaking immediately. As doping levels increased, the stiffness and brittleness increased. That is, the 20% and 50% doped gels were stiffer and did not deform as easily under pressure. The 20% and 50% gels were brittle and could only stretch minimally without breaking as compared to the lower-doped gels. When only an edge of the gel was fixed in place, and gravity was allowed to pull the opposite edge downward, the 20% and 50% gels did not bend under gravity as much as the lower percentage groups (e.g., the non-held edge of the 20% and 50% gels did not deflect as much as the control, 2%, 5%, or 10% gels).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments unless the embodiment is inoperative without those elements.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A sealant, comprising:

an electrophilic component comprising a first electrophilic material having a first functionality of a first reactive group;

a nucleophilic component comprising a first nucleophilic material having a second functionality of a second reactive group; and a doping component comprising: a second electrophilic material having a greater number of first reactive groups than the first electrophilic material; and/or a second nucleophilic material having a greater number of second reactive groups than the first nucleophilic material, wherein the doping component is present in an amount sufficient to provide a 2-20% molar contribution of the first reactive group and/or the second reactive group in the sealant; and wherein the electrophilic component, nucleophilic component, and doping component, when combined, produce a sealant; and wherein: (a) the first electrophilic material is a 4-arm multi-arm PEG and the second electrophilic material is a 6-arm or 8-arm multi-arm PEG; and/or (b) the first nucleophilic material is a 4-arm multi-arm PEG and the second nucleophilic material is a 6-arm or 8-arm multi-arm PEG.

2. The sealant according to claim 1, wherein the first multi-arm nucleophilic PEG is bioabsorbable in vivo.

3. The sealant according to claim 1, wherein the first multi-arm nucleophilic PEG is a PEG-Amine.

4. The sealant according to claim 3, wherein the PEG-Amine is 4-arm PEG-NH2-HCl.

5. The sealant according to claim 1, wherein the second nucleophilic material is a second multi-arm nucleophilic PEG.

6. The sealant according to claim 5, wherein the second multi-arm nucleophilic PEG is bioabsorbable in vivo.

7. The sealant according to claim 5, wherein the second multi-arm nucleophilic PEG of the doping component is a 6- and/or 8-arm PEG-NH2-HCl.

8. The sealant according to claim 1, wherein the first electrophilic material is a first multi-arm electrophilic PEG.

9. The sealant according to claim 8, wherein the first multi-arm electrophilic PEG is bioabsorbable in vivo.

10. The sealant according to claim 8, wherein the first multi-arm electrophilic PEG is a PEG-NHS Ester.

11. The sealant according to claim 10, wherein the PEG-NHS ester is 4-arm PEG-succinimidyl glutarate (SG).

12. The sealant according to claim 8, wherein the second electrophilic material is a second multi-arm electrophilic PEG.

13. The sealant according to claim 12, wherein the second multi-arm electrophilic PEG is bioabsorbable in vivo.

14. The sealant according to claim 12, wherein the second multi-arm electrophilic PEG of the doping component is a 6- and/or 8-arm PEG-SG.

15. The sealant according to claim 1, wherein the electrophilic component, the nucleophilic component, and/or the doping component further comprise an antioxidant.

16. The sealant according to claim 1, wherein the electrophilic component, the nucleophilic component, and/or the doping component further comprises a colorant.

17. The sealant according to claim 1, further comprising a contrast agent.

18. A system, comprising:

a sealant according to claim 1;

an applicator having an applicator body configured to hold a first component comprising a first electrophilic material in a first volume of space, and hold a second component comprising a first nucleophilic material in a second volume of space separate from the first volume of space, the applicator configured to allow the first component and second component to be combined.

19. A kit for preparing a sealant, comprising:

a first storage container including a dry first nucleophilic polymer powder;

a second storage container including an alkaline buffer for preparing a first nucleophilic polymer composition;

a third storage container including a dry first electrophilic polymer powder;

a fourth storage container including an acidic buffer for preparing a first electrophilic polymer composition;

at least one additional container, including:

a storage container including a dry second nucleophilic polymer powder; and/or a storage container including a dry second electrophilic polymer powder;

wherein the sealant is formed after combining the first nucleophilic polymer composition and first electrophilic polymer composition.

* * * * *